(12) United States Patent
Desmazeau et al.

(10) Patent No.: US 6,562,852 B2
(45) Date of Patent: May 13, 2003

(54) STREPTOGRAMIN DERIVATIVES, THEIR PREPARATION AND COMPOSITIONS WHICH CONTAIN THEM

(75) Inventors: Pascal Desmazeau, Tigery (FR); Baptiste Ronan, Clamart (FR); Eric Bacque, Morsang sur Orge (FR); Jean-Claude Barriere, Bures sur Yvette (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 10/024,698

(22) Filed: Dec. 21, 2001

(65) Prior Publication Data

US 2002/0156273 A1 Oct. 24, 2002

Related U.S. Application Data

(60) Provisional application No. 60/262,637, filed on Jan. 22, 2001.

(30) Foreign Application Priority Data

Dec. 21, 2000 (FR) ............................. 00 16804

(51) Int. Cl.[7] .................. C07D 498/22; C07D 498/18; A61K 31/42
(52) U.S. Cl. ....................... 514/375; 540/457
(58) Field of Search .......................... 540/457; 514/375

*Primary Examiner*—Bruck Kifle
(74) *Attorney, Agent, or Firm*—Finnegan, Henderson, Farabow, Garrett & Dunner, L.L.P.

(57) ABSTRACT

Group A streptogramin derivatives of formula (I) and salts thereof:

(I)

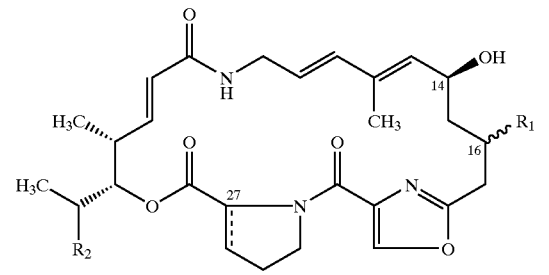

Group A streptogramin derivatives of formula (II) and salts thereof:

(II)

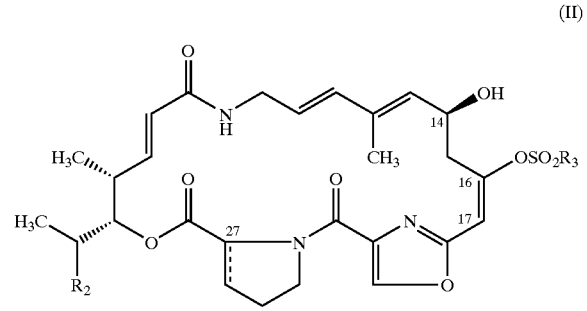

and Group A streptogramin derivatives of formula (III) and salts thereof:

(III)

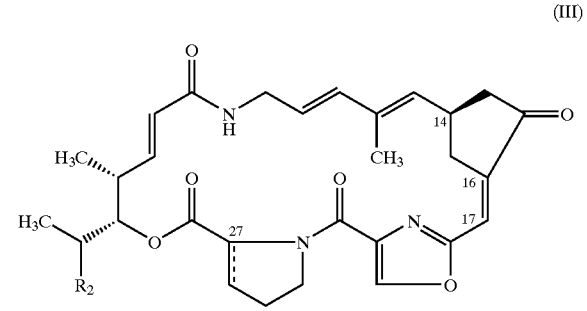

as well as processes for preparing such streptogramins, and pharmaceutical compositions comprising such streptogramins, alone or combined with at least one group B streptogramin derivative.

11 Claims, No Drawings

STREPTOGRAMIN DERIVATIVES, THEIR PREPARATION AND COMPOSITIONS WHICH CONTAIN THEM

Under the provisions of Section 119 of 35 U.S.C., Applicants hereby claim the benefit of French Application No. 00/16804, filed Dec. 21, 2000, which is incorporated herein by reference. Applicants also claim the benefit of U.S. Provisional Application No. 60/262,637, filed Jan. 22, 2001, which is incorporated herein by reference.

The present invention relates to group A streptogramin derivatives of formula (I):

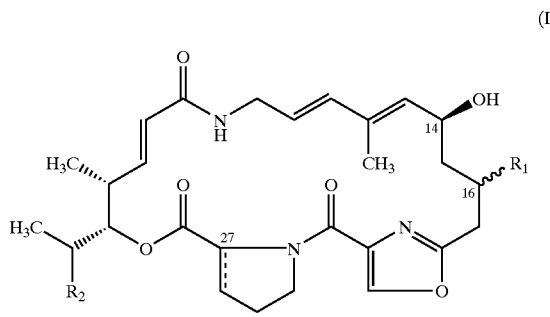

(I)

which have advantageous antibacterial activity.

Among the known streptogramins, pristinamycin (RP 7293), an antibacterial agent of natural origin produced by *Streptomyces pristinaespiralis*, was isolated for the first time in 1955. The pristinamycin sold under the name Pyostacine® comprises mainly pristinamycin IIA combined with pristinamycin IA.

Another antibacterial agent of the streptogramin class, virginiamycin, was isolated from *Streptomyces virginiae*, ATCC 13161 [Antibiotics and Chemotherapy, 5, 632 (1955)]. Virginiamycin (Staphylomycine®) comprises mainly factor $M_1$ (VM1) combined with factor S (VS).

The inventors have now discovered that the group A streptogramin derivatives of formula (I), wherein:

$R_1$ is chosen from cyano and ethynyl groups, $R_2$ is chosen from a hydrogen atom, a methyl group, and an ethyl group, and the bond ... is a single bond (27R stereochemistry) or a double bond, have advantageous antibacterial activity, alone or when combined with at least one group B streptogramin derivative.

The streptogramin derivatives of formula (I) may be prepared, for example, by known, art-recognized methods. Such methods include reacting a 16-sulphonyloxy derivative of formula (II):

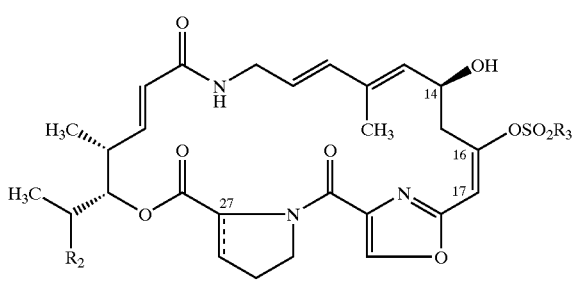

(II)

wherein:

$R_2$ is chosen from a hydrogen atom, a methyl group, and an ethyl group, $R_3$ is a perfluoroalkyl group comprising from 1 to 10 carbon atoms, and the bond ... is a single bond (27R stereochemistry) or a double bond, with an alkali metal cyanide, reducing the compound obtained from that reaction, and optionally separating the 16R and 16S isomers obtained. Another method includes carbonylating an above-defined 16-sulphonyloxy derivative of formula (II) to form a lactone, reducing the lactone to a lactol, reacting the compound formed, i.e., the lactol, with dimethyl diazomethylphosphonate or dimethyl 1-diazo-2-oxopropylphosphonate, and optionally separating the 16R and 16S isomers obtained.

In one embodiment, the $R_3$ group is chosen from a trifluoromethyl group and a nonafluorobutyl group.

In one embodiment, the alkali metal cyanide may be chosen from potassium cyanide, sodium cyanide, and caesium cyanide.

The cyanation reaction can be carried out, for example, in the presence of a palladium derivative, for example, tetrakis (triphenylphosphine)-palladium, and copper iodide. The process can be performed, for example, in an organic solvent, such as, a nitrile (for example, acetonitrile), an ether (for example, tetrahydrofuran), an amide (for example, dimethylformamide or N-methylpyrrolidinone), at a temperature ranging, for example, from 20° C. to the reflux temperature of the reaction mixture. The process can also be performed under an inert atmosphere, for example, argon or nitrogen.

The subsequent reduction may be carried out electrochemically, under an inert atmosphere, at a temperature of about 20° C., working in a buffer solution, such as, a solution degassed with argon, of tetraethylammonium tetrafluoroborate, tetraethylammonium acetate and acetic acid, under a potential difference of about −1.5 V (I=250 mA). Example 2 below gives a more detailed assessment of the operating conditions which may be used.

Such a reaction can lead to a mixture of the 16R and 16S isomers, which may be separated according to known, art-recognized methods which do not affect the rest of the molecule. For example, the separation of the epimer forms may be carried out by chromatography, such as, High Performance Liquid Chromatography (HPLC) on normal or reverse phase, HPLC on a chiral or non-chiral phase, or by flash chromatography, by crystallization, by centrifugal partition chromatography (CPC), or by any other appropriate separation technique available in the art.

The carbonylation reaction can be carried out under an atmosphere of carbon monoxide, such as, under one atmosphere, in the presence of a palladium derivative, for example, tetrakis(triphenylphosphine)-palladium, anhydrous lithium chloride and a base such as an alkali metal carbonate or alkaline-earth metal carbonate, for example, potassium carbonate, sodium carbonate, or caesium carbonate, in an inert organic solvent, such as an ether (for example, tetrahydrofuran), a nitrile (for example, acetonitrile), an amide (for example, dimethylformamide or N-methylpyrrolidinone), at a temperature ranging, for example, from 0° C. to the reflux temperature of the reaction mixture. In one embodiment of the process, the reaction can be performed at about 20° C.

The carbonylation reaction leads to the formation of a lactone of formula (III):

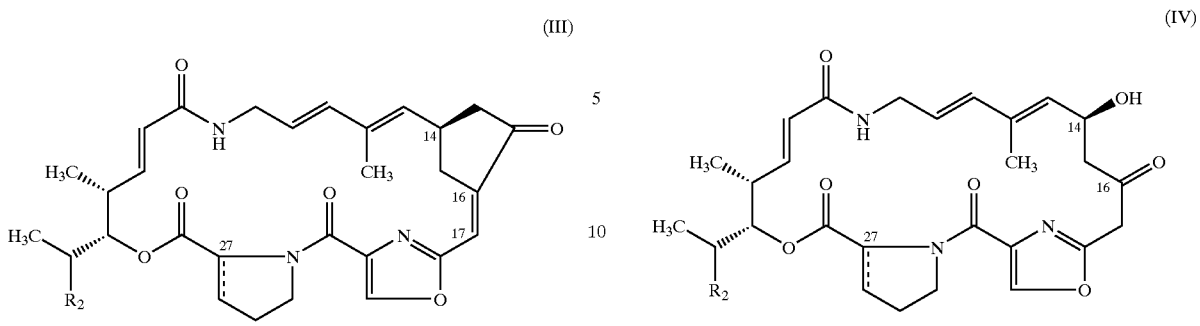

(III)

(IV)

wherein:

R₂ is chosen from a hydrogen atom, a methyl group, and an ethyl group, and the bond --- is a single bond (27R stereochemistry) or a double bond.

In one embodiment, the lactone can be reduced to a lactol saturated at 16,17 and then reacted with dimethyl diazomethylphosphonate or dimethyl 1-diazo-2-oxopropylphosphonate to form an ethynyl derivative.

The reduction of the lactone to a lactol may be carried out in the presence of a hydride such as, for example, lithium or potassium tri-sec-butylborohydride (L or K Selectride), in an inert organic solvent, such as an ether (for example, tetrahydrofuran) at a temperature ranging, for example, from −60° C. to 20° C., such as, at about −20° C., and under an inert atmosphere (for example, nitrogen or argon).

The reaction of dimethyl diazomethylphosphonate or dimethyl 1-diazo-2-oxopropylphosphonate can be carried out by applying the methods described by H. J. Bestmann et al., Synleft, 521 (1996) or by K. C. Nicolaou, Tetrahedron, 50(39), 11391 (1994), the relevant methods thereof are incorporated herein by reference. Such methods include a process performed in an inert solvent, such as, an ether (for example, tetrahydrofuran) or an alcohol (for example, methanol), at a temperature ranging, for example, from −78° C. to 40° C., such as, at about 20° C. The process can be performed under an inert atmosphere (for example, argon or nitrogen).

The reaction can also lead to a mixture of the 16R and 16S isomers, which may be separated according to known, art-recognized methods which do not affect the rest of the molecule. Such methods can, for example, include chromatography, such as, High Performance Liquid Chromatography (HPLC) on normal or reverse phase, HPLC on a chiral or non-chiral phase, and flash chromatography. Crystallization, centrifugal partition chromatography (CPC), or any other appropriate separation technique available in the art can also be used.

Streptogramin derivatives of formula (II) may be obtained, for example, by reacting a fluoride or anhydride, wherein the fluoride or anhydride comprises a perfluoroalkyl group comprising 1 to 10 carbon atoms, with a streptogramin derivative of formula (IV):

wherein:

R₂ is chosen from a hydrogen atom, a methyl group, and an ethyl group, and the bond --- is a single bond (27R stereochemistry) or a double bond, in the presence of a base, such as, a tertiary amine (for example, diisopropylethylamine or triethylamine), in an inert organic solvent, such as, a chlorinated solvent (for example, dichloromethane), an ether (for example, tetrahydrofuran) or an amide (for example, dimethylformamide) at a temperature ranging from −78° C. to 20° C., such as, at about −70° C., and under an inert atmosphere (for example, argon or nitrogen).

In one embodiment, the sulphonic anhydride (for example, triflic anhydride) or the sulphonyl fluoride (for example, perfluoro-1-butanesulphonyl fluoride) corresponding to the selected R₃ group can be reacted.

The pristinamycin derivatives of formula (IV) correspond, respectively, to pristinamycin IIA (PIIA), pristinamycin IIB (PIIB), pristinamycin IIC (PIIC), pristinamycin IID (PIID), pristinamycin IIF (PIIF) and pristinamycin IIG (PIIG), which are known components of natural pristinamycin. The components PIIF and PIIG have been disclosed in European patent application no. EP-A-0 614 910. Pristinamycin IIC (PIIC) and pristinamycin IID (PIID) may be obtained as described by J. C. Barriére et al., Expert. Opin. Invest. Drugs, 3(2),115–31 (1994).

The preparation and separation of natural group A streptogramin components, such as, streptogramins of formula (IV), can be carried out by fermentation and isolation of the constituents from the fermentation must according to or by analogy with the method described by J. Preud'homme et al., Bull. Soc. Chim. Fr., vol. 2, 585 (1968), or in European patent application no. EP-A-0 614 910. Additionally, the preparation of natural group A components may be carried out, for example, by specific fermentation, as disclosed in French patent application no. FR-A-2 689 518.

The group A streptogramin derivatives of formulae (II) and (III) are novel products that are useful for preparing streptogramin derivatives according to the invention.

The streptogramin derivatives of formula (I) may be purified, when appropriate, by physical methods, such as, crystallization, chromatography, and CPC.

The streptogramin derivatives according to the present invention have superior antibacterial properties and synergistic properties with respect to the antibacterial activity of the group B streptogramin derivatives. They are notably advantageous on account of their powerful activity, alone or in combination.

When at least one group A streptogramin derivative of the invention is combined with at least one group B streptogramin component or derivative, this component or derivative may be chosen, depending on whether it is desired to obtain a form for oral or parenteral administration, from the following natural components: pristinamycin IA, pristinamycin IB, pristinamycin IC, pristinamycin ID, pristinamycin IE, pristinamycin IF, pristinamycin IG, virginiamycin S1, S3 or S4, vernamycin B or C, etamycin or from semisynthetic derivatives as disclosed in U.S. Pat. Nos. or European patent application nos. U.S. Pat. Nos. 5,618,599, 4,798,827, 5,326,782, EP-A-0 772 630 and EP-A-0 770 132.

Representative group B streptogramin components and derivatives may include, for example, (I) streptogramin derivatives of formula (A), and salts thereof:

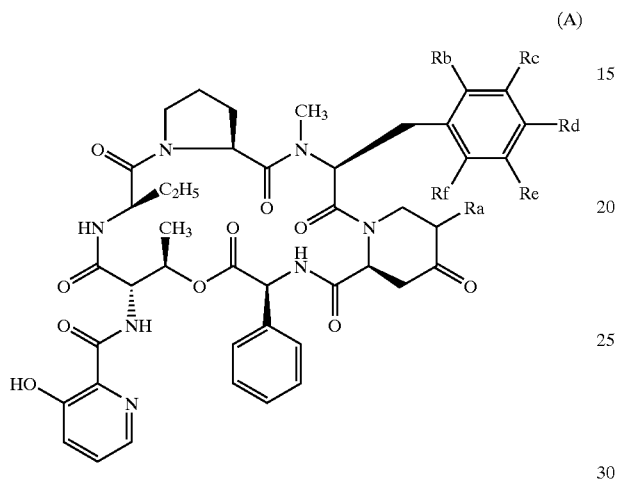

(A)

wherein:
(1) Rb, Rc, Re, and Rf are each a hydrogen atom;
Rd is chosen from a hydrogen atom and a dimethylamino group; and
Ra is chosen from:
(A) —$CH_2R'a$ groups, wherein R'a is chosen from:
(i) a pyrrolidinyl-3-thio group,
(ii) a piperidyl-3-thio group,
(iii) a piperidyl-4-thio group,
wherein groups (i)–(iii) may be unsubstituted or substituted with at least one group chosen from alkyl groups, and
(iv) alkylthio groups which are substituted with 1 or 2 groups chosen from:
(a) a hydroxysulfonyl group,
(b) alkylamino groups,
(c) dialkylamino groups, which may be unsubstituted or substituted with at least one group chosen from a mercapto group or dialkylamino groups,
(d) a piperazine ring which may be substituted or unsubstituted, a morpholino group, a thiomorpholino group, a piperidino group, a 1-pyrrolidinyl group, a 2-piperidyl group, a 3-piperidyl group, a 4-piperidyl group, a 2-pyrrolidinyl group, and a 3-pyrrolidinyl group, each of which may be unsubstituted or substituted with at least one group chosen from alkyl groups, and
(B) =CHR'a groups, wherein R'a is chosen from:
(i) a pyrrolidinyl-3-amino group,
(ii) a piperidyl-3-amino group and a piperidyl-4-amino group,
(iii) a pyrrolidinyl-3-oxy group,
(iv) a piperidyl-3-oxy group and a piperidyl-4-oxy group,
(v) a pyrrolidinyl-3-thio group,
(vi) a piperidyl-3-thio group and a piperidyl-4-thio group,
wherein groups (i)–(vi) may be unsubstituted or substituted with at least one group chosen from alkyl groups,
(vii) alkylamino groups,
(viii) alkyloxy groups, and
(ix) alkylthio groups,
wherein groups (vii), (viii), and (ix) are substituted with 1 or 2 groups chosen from:
(a) a hydroxysulfonyl group,
(b) alkylamino groups,
(c) dialkylamino groups unsubstituted or substituted with at least one group chosen from dialkylamino groups,
(d) trialkylammonio groups,
(e) a 4-imidazolyl group, and a 5-imidazolyl group, each of which may be unsubstituted or substituted with at least one group chosen from alkyl groups,
(f) a piperazine ring which may be substituted or unsubstituted, a morpholino group, a thiomorpholino group, a piperidino group, a 1-pyrrolidinyl group, a 2-piperidyl group, a 3-piperidyl group, a 4-piperidyl group, a 2-pyrrolidinyl group, and a 3-pyrrolidinyl group, each of unsubstituted or substituted with at least one group chosen from alkyl groups,
(C) a quinuclidinyl-3-thiomethyl group, and
(D) a quinuclidinyl-4-thiomethyl group; or
(2) Ra is a hydrogen atom, and
(a) Rb, Re, and Rf are each a hydrogen atom, and
Rd is chosen from a —$NHCH_3$ group and a —$N(CH_3)_2$ group, and Rc is chosen from a chlorine atom and a bromine atom, or, when Rd is a —$N(CH_3)_2$ group, Rc is chosen from ($C_3$–$C_5$) alkenyl groups, or
(b) Rb, Rd, Re, and Rf are each a hydrogen atom, and
Rc is chosen from halogen atoms, aminomonoalkyl groups, aminodialkyl groups, alkyloxy groups, a trifluoromethyloxy group, thioalkyl groups, ($C_1$–$C_3$) alkyl groups, and trihalomethyl groups, or
(c) Rb, Rc, Re, and Rf are each a hydrogen atom, and
Rd is chosen from halogen atoms, an ethylamino group, a diethylamino group, a methylethylamino group, alkyloxy groups, a trifluoromethyloxy group, thioalkyl groups, ($C_1$–$C_6$) alkyl groups, aryl groups, and trihalomethyl groups, or
(d) Rb, Re, and Rf are each a hydrogen atom,
Rc is chosen from halogen atoms, aminomonoalkyl groups, aminodialkyl groups, alkyloxy groups, a trifluoromethyloxy group, thioalkyl groups, and ($C_1$–$C_3$) alkyl groups, and
Rd is chosen from halogen atoms, an amino group, aminomonoalkyl groups, aminodialkyl groups, alkyloxy groups, a trifluoromethyloxy group, thioalkyl groups, ($C_1$–$C_6$) alkyl groups, and trihalomethyl groups, or
(e) Rc, Re, and Rf are each a hydrogen atom, and
Rb and Rd are each a methyl group,
and further, for example, (II) semisynthetic group B streptogramin derivatives of formula (B), and salts thereof:

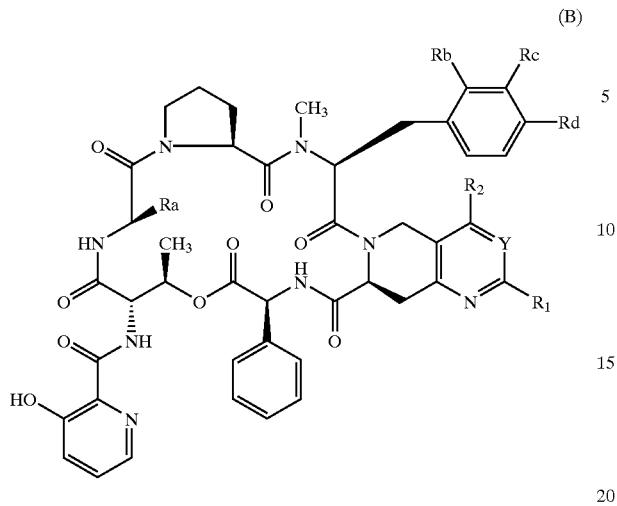

(B)

wherein:
(A) Y is chosen from (i) a nitrogen atom and (ii) =CR$_3$— groups, and
  (1) when Y is chosen from =CR$_3$— groups, R$_1$ is chosen from
    (a$_1$) a hydrogen atom, C$_1$–C$_8$ alkyl groups, and C$_2$–C$_8$ alkenyl groups,
    (b$_1$) C$_3$–C$_8$ cycloalkyl groups, and saturated and unsaturated 3- to 8-membered heterocyclyl groups,
    (c$_1$) an unsubstituted phenyl group,
    (d$_1$) a phenyl group substituted with at least one substituent chosen from halogen atoms, a hydroxyl group, alkyl groups, alkyloxy groups, alkylthio groups, alkylsulphinyl groups, alkylsulphonyl groups, an amino group, alkylamino groups, and dialkylamino groups, and
    (e$_1$) groups —NR'R", wherein:
      R' and R", which are identical or different, are each chosen from a hydrogen atom, and C$_1$–C$_3$ alkyl groups, or
      R' and R", form, together with the nitrogen atom to which they are attached, a 3- to 8-membered heterocyclyl group, wherein one of the members, in addition to the nitrogen atom, may be a heteroatom chosen from an oxygen atom, a sulphur atom, and a nitrogen atom, and wherein the heterocyclyl group is unsubstituted or substituted with a group chosen from alkyl groups, C$_2$–C$_8$ alkenyl groups, C$_3$–C$_6$ cycloalkyl groups, saturated and unsaturated 4- to 6-membered heterocyclyl groups, a benzyl group, an unsubstituted phenyl group, and a substituted phenyl group, as defined above in (d$_1$),
    (f$_1$) halomethyl groups, a hydroxymethyl group, and alkyloxymethyl groups,
    (g$_1$) alkylthiomethyl groups, wherein the alkyl portion is unsubstituted or substituted with an —NR'R" group, and wherein R' and R" are as defined above in (e$_1$),
    (h$_1$) alkylsulphinylmethyl groups, alkylsulphonylmethyl groups, an acyloxymethyl group, a benzoyloxymethyl group, a cyclopropylaminomethyl group, and —(CH$_2$)$_n$NR'R" groups, wherein n is chosen from integers ranging from 1 to 4, and wherein R' and R" are as defined above in (e$_1$), and
    (i$_1$) when R$_3$ is a hydrogen atom, R$_1$ is additionally chosen from a formyl group, a carboxyl group, alkyloxycarbonyl groups, and —CONR'R" groups, wherein R' and R" are defined as above in (e$_1$), and
  (2) when Y is a nitrogen atom, R$_1$ is chosen from
    (a$_2$) options (a$_1$), (b$_1$), (c$_1$), (d$_1$), and (e$_1$) as defined above, and
    (b$_2$) XR° groups, wherein X is chosen from an oxygen atom, a sulphur atom, a sulphinyl group, a sulphonyl group, and an —NH— group, and wherein R° is chosen from (i) (C$_1$ to C$_8$) alkyl groups, (ii) (C$_3$ to C$_6$) cycloalkyl groups, (iii) saturated and unsaturated 3- to 8-membered heterocyclyl groups, (iv) 3- to 8-membered heterocyclylmethyl groups in which the heterocyclyl portion is attached to the methyl group by a carbon atom, (v) an unsubstituted phenyl group, (vi) phenyl groups substituted with at least one group chosen from halogen atoms, a hydroxyl group, alkyl groups, alkyloxy groups, alkylthio groups, alkylsulfinyl groups, alkylsulfonyl groups, an amino group, alkylamino groups, and dialkylamino groups, (vii) —(CH$_2$)$_n$NR'R" groups, wherein R' and R" are as defined above in (e$_1$), and wherein n is chosen from integers ranging from 2 to 4, and (viii) if X is an NH group, R° may also be a hydrogen atom;
(B) R$_2$ is chosen from a hydrogen atom and C$_1$–C$_3$ alkyl groups,
(C) R$_3$ is chosen from a hydrogen atom, alkyl groups, a carboxyl group, alkyloxycarbonyl groups, and carbamoyl groups of formula —CO—NR'R", wherein R' and R" are defined as above in (e$_1$),
(D) Ra is chosen from a methyl group and an ethyl group, and
(E) Rb, Rc, and Rd are defined as follows:
  (1) Rb and Rc are each a hydrogen atom, and Rd is chosen from a hydrogen atom, a methylamino group, and a dimethylamino group, or
  (2) Rb is a hydrogen atom,
  Rc is chosen from a hydrogen atom, a chlorine atom, a bromine atom, and C$_3$–C$_5$ alkenyl groups, and
  Rd is chosen from —N(CH$_3$)R''' groups, wherein R''' is chosen from
    (a) alkyl groups,
    (b) C$_2$–C$_4$ hydroxyalkyl groups,
    (c) C$_2$–C$_8$ alkenyl groups, wherein the C$_2$–C$_8$ alkenyl groups are unsubstituted or substituted with (i) an unsubstituted phenyl group, (ii) a cycloalkyl (C$_3$–C$_6$)methyl group, (iii) an unsubstituted benzyl group, (iv) a benzyl group substituted with at least one substituent chosen from halogen atoms, a hydroxyl group, alkyl groups, alkyloxy groups, alkylthio groups, alkylsulphinyl groups, alkylsulphonyl groups, an amino group, alkylamino groups, and dialkylamino groups, or (v) heterocyclylmethyl groups and heterocyclylethyl groups, wherein the heterocyclyl portions of the heterocyclylmethyl groups and the heterocyclylethyl groups are chosen from saturated and unsaturated 5- to 6-membered heterocyclyl groups comprising from 1 to 2 heteroatoms chosen from a sulphur atom, an oxygen atom, and a nitrogen atom, and wherein the heterocyclyl groups may be unsubstituted or substituted with a group chosen from alkyl groups, C$_2$–C$_8$ alkenyl groups, C$_3$–C$_6$ cycloalkyl groups, saturated and unsaturated 4- to 6-membered heterocyclyl groups, an unsubstituted phenyl group, a benzyl group, or a substituted phenyl group as defined above in (d₁),
(d) a cyanomethyl group,
(e) —CH₂CORe groups, wherein Re is chosen from
  (i) —OR'e groups, wherein R'e is chosen from a hydrogen atom, C₁–C₆ alkyl groups, C₂–C₆ alkenyl groups, a benzyl group, and heterocyclylmethyl groups, wherein the heterocyclyl portion is chosen from 5- to 6-membered heterocyclyl groups comprising from 1 to 2 heteroatoms chosen from a sulphur atom, an oxygen atom, and a nitrogen atom, (ii) alkylamino groups, alkylmethylamino groups, heterocyclylamino groups and heterocyclylmethylamino groups, wherein the heterocyclyl portion of the heterocyclylamino groups and the heterocyclylmethylamino groups is chosen from 5- to 6-membered saturated heterocyclyl groups comprising from 1 to 2 heteroatoms chosen from a sulphur atom, an oxygen atom, and a nitrogen atom, and wherein the heterocyclyl groups may be unsubstituted or substituted with a group chosen from alkyl groups, a benzyl group, and alkyloxycarbonyl groups, or
(3) Rb is a hydrogen atom,
Rd is chosen from an —NHCH₃ group and an —N(CH₃)₂ group, and
Rc is chosen from a chlorine atom, and a bromine atom, and when Rd is an —N(CH₃)₂ group, Rc is chosen from C₃–C₅ alkenyl groups, or
(4) Rb and Rd are each a hydrogen atom, and
Rc is chosen from halogen atoms, alkylamino groups, dialkylamino groups, alkyloxy groups, a trifluoromethoxy group, thioalkyl groups, C₁–C₆ alkyl groups, and trihalomethyl groups, or
(5) Rb and Rc are each a hydrogen atom, and
Rd is chosen from halogen atoms, an ethylamino group, a diethylamino group, a methylethylamino group, alkyloxy groups, a trifluoromethoxy group, alkylthio groups, alkylsulphinyl groups, alkylsulphonyl groups, C₁–C₆ alkyl groups, a phenyl group, and trihalomethyl groups, or
(6) Rb is a hydrogen atom, and
Rc is chosen from halogen atoms, alkylamino groups, dialkylamino groups, alkyloxy groups, a trifluoromethoxy group, thioalkyl groups, and C₁–C₃ alkyl groups, and
Rd is chosen from halogen atoms, an amino group, alkylamino groups, dialkylamino groups, alkyloxy groups, a trifluoromethoxy group, thioalkyl groups, C₁–C₆ alkyl groups, and trihalomethyl groups, or
(7) Rc is a hydrogen atom, and
Rb and Rd are each a methyl group, and even further, for example, (III) semisynthetic group B derivatives of formula (C), and salts thereof, when salts exists:

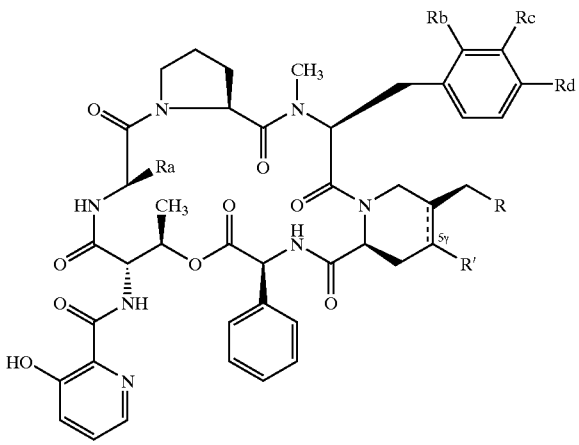

wherein:
(A) R is chosen from
  (1) —NR₁R₂ groups, wherein R₁ and R₂, which may be identical or different, are each chosen from
    (i) a hydrogen atom,
    (ii) (C₁–C₈) alkyl groups,
    (iii) (C₁–C₈) alkyl groups substituted with a hydroxyl group,
    (iv) (C₃–C₈) alkenyl groups,
    (v) (C₃–C₈) cycloalkyl groups,
    (vi) (C₁–C₈) alkyloxy groups,
    (vii) dialkylamino groups,
    (viii) phenylalkyl groups,
    (ix) phenylalkyl groups substituted with at least one group chosen from halogen atoms, alkyl groups, hydroxyalkyl groups, alkyloxy groups, and dialkylamino groups, and
    (x) 3- to 8-membered saturated and unsaturated heterocyclylalkyl groups comprising at least one hetero atom chosen from nitrogen, oxygen, and sulphur, or
    (xi) R₁ and R₂ form, together with the nitrogen atom to which they are attached, a saturated, partially saturated or unsaturated mono- or polycyclic 3- to 12-membered heterocycle group, wherein one of the members, in addition to the nitrogen atom, may be an atom chosen from oxygen, sulphur, and nitrogen, and wherein the heterocyclyl group is unsubstituted or substituted with at least one group chosen from a hydroxyl group, alkyl groups, an unsubstituted phenyl group, a phenyl group substituted with a halogen atom, phenylalkyl groups, phenyl(C₂–C₄) alkenyl groups, hydroxyalkyl groups, acyl groups, alkyloxycarbonyl groups, heterocyclyl groups and heterocyclylcarbonyl groups, wherein the heterocyclyl portion is saturated or unsaturated (4- to 6-membered) and comprises at least one hetero atom chosen from nitrogen, sulphur, and oxygen, and
  (2) —SR₃ groups, wherein R₃ is chosen from
    (i) (C₁–C₈) alkyl groups and (C₃–C₈) cycloalkyl groups substituted with —NR₁R₂, wherein R₁ and R₂, which may be identical or different, are each chosen from a hydrogen atom and alkyl groups, or form, together with the nitrogen atom to which they are attached, a heterocycle as defined in (xi) above, and (ii) 3- to 7-membered saturated and unsaturated heterocyclyl and heterocyclylmethyl groups, wherein one of the members, in addition to the nitrogen atom, may be a heteroatom chosen from oxygen, sulphur, and nitrogen, and wherein the heterocyclyl portion is unsubstituted or substituted with at least one group chosen from alkyl groups, (B)

is a residue of an unsaturated ring which is not substituted in the 5γ position

or the residue of a saturated ring which is substituted in the 5γ position with a fluorine atom

(C) Ra is chosen from a methyl group and an ethyl group, and
(D) Rb, Rc and Rd are defined below:
  1) Rb and Rc are each a hydrogen atom, and Rd is chosen from a hydrogen atom, a methylamino group, and a dimethylamino group, or
  2) Rb is a hydrogen atom, Rc is chosen from a hydrogen atom, a chlorine atom, a bromine atom, and a ($C_3$ to $C_5$) alkenyl group, and Rd is —N(CH$_3$)—R''', wherein R''' is chosen from:
    (1) alkyl groups, (2) ($C_2$ to $C_4$) hydroxyalkyl groups, (3) ($C_2$ to $C_8$) alkenyl groups, (4) phenylalkenyl groups, (5) cycloalkyl($C_3$ to $C_6$)methyl groups, (6) an unsubstituted benzyl group, (7) a substituted benzyl group, (8) heterocyclylmethyl groups and heterocyclylethyl groups, (9) a —CH$_2$CN group, (10) a —CH$_2$COOH group, and (11) —CORe groups and —CH$_2$CORe groups for which either:
      (a) Re is —OR'e, wherein R'e is chosen from a hydrogen atom, $C_1$–$C_6$ alkyl groups, $C_2$–$C_6$ alkenyl groups, a benzyl group, and heterocyclylmethyl groups, wherein the heterocyclyl portion is chosen from 5- to 6-membered heterocyclyl groups comprising from 1 to 2 heteroatoms chosen from a sulphur atom, an oxygen atom, and a nitrogen atom, or
      (b) Re is chosen from alkylamino groups, alkylmethylamino groups, heterocyclylamino groups, and heterocyclylmethylamino groups, or
  3) Rb is a hydrogen atom,
    Rd is chosen from an —NHCH$_3$ group and an —N(CH$_3$)$_2$ group, and
    Rc is chosen from a chlorine atom, and a bromine atom, and when Rd is an —N(CH$_3$)$_2$ group, Rc is chosen from $C_3$–$C_5$ alkenyl groups, or
  4) Rb and Rd are each a hydrogen atom, and
    Rc is chosen from halogen atoms, alkylamino groups, dialkylamino groups, alkyloxy groups, a trifluoromethoxy group, thioalkyl groups, ($C_1$–$C_6$) alkyl groups, and trihalomethyl groups, or
  5) Rb and Rc are each a hydrogen atom, and
    Rd is chosen from halogen atoms, an ethylamino group, a diethylamino group, a methylethylamino group, alkyloxy groups, a trifluoromethoxy group, alkylthio groups, alkylsulphinyl groups, alkylsulphonyl groups, ($C_1$–$C_6$) alkyl groups, a phenyl group, and trihalomethyl groups, or
  6) Rb is a hydrogen atom,
    Rc is chosen from halogen atoms, alkylamino groups, dialkylamino groups, alkyloxy groups, a trifluoromethoxy group, thioalkyl groups, ($C_1$–$C_3$) alkyl groups, and
    Rd is chosen from halogen atoms, an amino group, alkylamino groups, dialkylamino groups, alkyloxy groups, a trifluoromethoxy group, thioalkyl groups, ($C_1$–$C_6$) alkyl groups, and trihalomethyl groups, or
  7) Rc is a hydrogen atom, and
    Rb and Rd are each a methyl group.

It is understood that the combinations formed from the derivatives according to the invention and from group B streptogramins also fall within the context of the present invention.

The group B streptogramin derivatives of formula (B) may be prepared, for example, according to the methods disclosed in International patent application no. PCT/FR 99/00409. The group B streptogramin derivatives of formula (C) may be prepared, for example, according to the methods disclosed in International patent application no. PCT/FR 00/02146.

In vitro on *Staphylococcus aureus* IP8203, the streptogramin derivatives according to the invention have been shown to be active at concentrations of between 0.015 and 32 μg/ml, alone or combined with a group B derivative such as pristinamycin IB. In vivo, the streptogramin derivatives according to the invention synergized the antimicrobial activity of pristinamycin I$_B$ or of semisynthetic derivatives of formula (C) on experimental infections of mice with *Staphylococcus aureus* IP8203 at doses ranging, for example, from 72 to 150 mg/kg orally (DC$_{50}$).

The compounds according to the invention are advantageous on account of their low toxicity. None of the compounds of the invention have shown any toxicity at doses of 150 mg/kg on *Staphylococcus aureus* IP8203, when administered twice a day subcutaneously or orally in mice.

Representative group A streptogramin derivatives of formula (I), which may be used according to the invention, for example, include streptogramin derivatives of formula (I), wherein:
  $R_1$ is chosen from a cyano group and an ethynyl group,
  $R_2$ is a methyl group, and
  the bond ‒‒‒ is a single bond (27R stereochemistry) or a double bond, are advantageous. The compounds described below in the Examples are exemplary of such derivatives.

Representative group A streptogramin derivatives of formula (I), which may be used according to the invention, for example, include the compounds mentioned below in the examples, and the following compounds:
  (16R)-16-deoxo-16-ethynylpristinamycin II$_A$
  (16S)-16-deoxo-16-ethynylpristinamycin II$_A$
  (16R)-16-cyano-16-deoxopristinamycin II$_A$
  (16S)-16-cyano-16-deoxopristinamycin II$_A$ The examples which follow, given without any implied limitation, illustrate the present invention.

In the examples which follow, the 16-deoxopristinamycin IIA (or IIB) nomenclature indicates the replacement of the ketone function in position 16 with 2 hydrogen atoms. As the chromatography proceeded, all the fractions were analyzed by thin layer chromatography (TLC) on Merck 60F254 silica plates. The fractions corresponding to the same spot on TLC were combined and then concentrated to dryness, under reduced pressure (30° C.; 2.7 kPa). The residues thus obtained were analyzed by known, art-recognized spectroscopic techniques (such as, NMR, IR, and MS), allowing the expected product to be identified.

EXAMPLE 1

16-Deoxo-16-ethynylpristinamycin II$_B$: (mixture of the 16R and 16S isomers in 70/30 proportions)

0.415 g of potassium carbonate and 0.35 g of dimethyl 1-diazo-2-oxopropylphosphonate were added, at 20° C. under an argon atmosphere, to 0.8 g of (16R)-16-deoxo-14, 16-butyrolactolpristinamycin II$_B$ dissolved in 40 cm$^3$ of methanol. After stirring overnight, the reaction mixture was diluted with 100 cm$^3$ of dichloromethane and then washed with 70 cm$^3$ of saturated aqueous sodium bicarbonate solution. The organic phase was separated out after settling had taken place, concentrated under reduced pressure (2.7 kPa) to 30 cm$^3$ and the residue was diluted by adding 70 cm$^3$ of dichloromethane. The solution obtained was washed with 40 cm$^3$ of water. The organic phase was separated out after settling had taken place, dried over magnesium sulphate, filtered and then concentrated to dryness under reduced pressure (2.7 kPa) to give 0.8 g of a pale yellow foam, which was purified by flash chromatography on silica [eluent: dichloromethane/acetonitrile/methanol (95/12.5/2.5 by volume)]. After concentrating the fractions containing the expected product, a solid was obtained, which was stirred in 15 cm$^3$ of diisopropyl ether and then filtered off and dried under reduced pressure (2.7 kPa) to give 0.27 g of 16-deoxo-16-ethynylpristinamycin II$_B$ (mixture of the 16R and 16S isomers in 70/30 proportions), in the form of a white solid that melted at about 128° C. with decomposition.

$^1$H NMR spectrum (300 MHz, CDCl$_3$, δ in ppm). We observed a mixture of the (16R) and (16S) isomers in 70/30 proportions.
0.96(d, J=6.5 Hz:3H); 1.00(mt:3H); 1.09(mt:3H); from 1.45 to 1.60 and 1.70 to 2.30(2 series of mt:7H); 1.82 and 1.87(2s:3H in total); 2.14 and 2.24(2d, J=2 Hz:1H in total); 2.75(mt:1 H); from 2.75 to 2.90 and from 2.95 to 3.15(2 series of mt:3 H in total); from 3.35 to 3.65(mt:1H in total); from 3.75 to 3.95 and 4.08(2 series of mt:2H in total); 4.50(mt:1H); from 4.70 to 4.90(mt:3H);5.35 and 5.52(2 broad d, J=9 Hz:1H in total); from 5.60 to 5.85(mt:1H); 5.83(dd, J=16.5 and 1.5 Hz:1H); 5.90 and 5.99(2 mts:1H in total); 6.18 and 6.20(2d, J=16 Hz:1H in total); 6.48 and 6.51 (2 dd, J=16.5 and 5Hz:1H in total); 8.09 and 8.11(2s:1H in total).

The 16R and 16S isomers were separated by high performance liquid chromatography on a stationary silica phase (preparative column:80×350 mm; stationary phase: Hypersil 8 μm silica; mobile phase: CH$_2$Cl$_2$ 46%+50% heptane+2% MeOH+2% CH$_3$CN; flow rate: 100 ml/min; detection: UV 265 nm). A solution of 1.1 g of 16-deoxo-16-ethynylpristinamycin II$_B$ (mixture of the 16R and 16S isomers in 70/30 proportions) in 100 cm$^3$ of dichloromethane was injected onto the preparative column. The entire operation was repeated a second time on an identical solution. After concentrating the fractions containing the A isomer, 0.99 g of the A isomer of 16-deoxo-16-ethynylpristinamycin II$_B$ was obtained in the form of a white powder.

A isomer: $^1$H NMR spectrum (400 MHz, CDCl$_3$, δ in ppm): 0.97(d, J=6.5 Hz:3H); 1.01(d, J=6.5 Hz:3H); 1.10(d, J=6.5 Hz:3H); 1.56(mt:1H); from 1.75 to 2.05(mt:5H); 1.87(s:3H); from 2.05 to 2.15(mt:1H); 2.15(d, J=2Hz: 1H); 2.77(mt:1H); 2.81(dd, J=16 and 8 Hz:1H); 3.04(mt:1H); 3.10(dd, J=16and 6.5 Hz:1H); 3.54(mt:1H); 3.88(mt:1H); 4.09(mt:1H); 4.52(mt:1H); from 4.75 to 4.85 (mt:3H); 5.36 (broad d, J=9 Hz:1H); 5.76(ddd, J=16–8 and 4 Hz:1H); 5.83(broad d, J=16.5 Hz:1H); 6.02(mt:1H); 6.21(d, J=16 Hz:1H); 6.52(dd, J=16.5 and 5 Hz:1H); 8.10(s:1H).

After concentrating the fractions containing the B isomer, 0.5 g of the B isomer of 16-deoxo-16-ethynylpristinamycin II$_B$ was obtained in the form of a white powder.

B isomer: $^1$H NMR spectrum (400 MHz, CDCl$_3$, δ in ppm): 0.97(d, J=6.5 Hz:3H); 1.01(d, J=6.5 Hz:3H); 1.09(d, J=6.5 Hz:3H); from 1.70 to 2.05 (mt:5H); 1.83(s:3H); from 2.05 to 2.20(mt:2H); 2.25(d, J=2 Hz:1H); 2.76(mt:1H) from 3.00 to 3.15 mt:3H); 3.40(mt:1H); from 3.80 to 4.00 (mt:2H); 4.51(mt:1H); from 4.70 to 4.85(mt:2H); 4.87 (mt:1H); 5.54(broad d, J=9 Hz:1H); 5.67(mt:1H); 5.79 (broad d, J=16.5 Hz:1H); 5.91(mt:1H); 6.19(d, J=16 Hz:1H); 6.49(dd, J=16.5 and 5 Hz:1H); 8.12(s:1H).

Dimethyl 1-diazo-2-oxopropylphosphonate was prepared according to Callant et al., Synth. Comm. (1984) p.155.

(16R)-16-Deoxo-14,16-butyrolactolpristinamycin II$_B$ was obtained in the following manner:

15.5 cm$^3$ of L-Selectride® were added slowly, at −20° C. under an argon atmosphere, to 4.18 g of 16,17-dehydro-16-deoxo-14,16-butyrolactonepristinamycin II$_B$ suspended in 84 cm$^3$ of tetrahydrofuran. After stirring for 1 hour, 1.7 cm$^3$ of acetic acid were added, followed by addition of 450 cm$^3$ of water. The reaction mixture was extracted 3 times with 120 cm$^3$ of ethyl acetate. The organic phases were combined, washed with 150 cm$^3$ of saturated aqueous sodium chloride solution, dried over magnesium sulphate, filtered and then concentrated to dryness under reduced pressure (2.7 kPa) and gave, after stirring in 150 cm$^3$ of diethyl ether, a white foam. After purification by flash chromatography on silica [eluent: dichloromethane/acetonitrile methanol (96/2/2 by volume)] and concentration of the fractions containing the expected products, 1.8 g of (16R)-16-deoxo-14,16-butyrolactolpristinamycin II$_B$ were obtained in the form of a white solid.

$^1$H NMR spectrum (400 MHz, CDCl$_3$, δ in ppm): 0.99(d, J=6.5 Hz:3H); 1.07(d, J=6.5 Hz:3H); 1.10(d, J=6.5 Hz:3H); from 1.65 to 2.25 (mt:6H); 1.73 (s:3H); 2.47(mt:1H); 2.66 (mt:1H); 2.79(mt:1H); 2.84(dd, J=16 and 4 Hz:1H); 3.01 (dd, J=16 and 7 Hz:1H); 3.56(mt:1H); 4.03(mt:1H); 4.10 (mt:1H); 4.56(mt:1 H); 4.70(dd, J=8 and 3 Hz:1H); 4.74(dd, J=10 and 1.5 Hz:1H); 5.08(mt:1H; from 5.35 to 5.45 (mt:2H); 5.74(ddd, J=16–5 and 4 Hz:1H); 5.83(dd, J=16.5 and 1.5 Hz:1H); 6.10(mt:1H); 6.19(d, J=16 Hz:1H); 6.52(dd, J=16.5 and 5 Hz:1H); 8.17 (s:1H).

16,17-Dehydro-16-deoxo-14,16-butyrolactonepristinamycin II$_B$ was prepared in the following manner:

1.47 g of tetrakis(triphenylphosphine)palladium, 3.37 g of lithium chloride and 8.8 g of potassium carbonate were added, at 20° C. under an argon atmosphere, to 21 g of 16,17-dehydro-16-trifluoromethanesulphonyloxy-pristinamycin II$_B$ dissolved in 250 cm$^3$ of tetrahydrofuran. Carbon monoxide was bubbled into the reaction mixture for 27 hours, after which 4.4 g of potassium carbonate were added and the bubbling of carbon monoxide into the reaction mixture was continued for 68 hours. The reaction mixture was filtered through Celite®, diluted with 250 cm$^3$ of dichloromethane and stirred with 200 cm$^3$ of saturated aqueous sodium chloride solution. After filtration through Celite®, the organic phase was washed twice with 200 cm$^3$ of saturated aqueous sodium chloride solution, dried over magnesium sulphate, filtered and then concentrated to dryness under reduced pressure (2.7 kPa) to give 13.5 g of 16,17-dehydro-16-deoxo-14,16-butyrolactonepristinamycin II$_B$ in the form of a yellow solid.

$^1$H NMR spectrum (400 MHz, CDCl$_3$, δ in ppm): 0.96(d, J=6.5 Hz:3H); 1.01(d, J=6.5 Hz:3H); 1.12(d, J=6.5 Hz:3H); from 1.65 to 2.05(mt:4H); 1.77 (s:3H); 2.17(mt:1H); 2.76 (mt:1H); from 3.30 to 3.45(mt:2H); 3.99(broad d, J=17 Hz: 1H); from 4.00 to 4.15(mt:2H); 4.46(mt:1H); 4.81(dd, J=10 and 1.5 Hz:1H); 4.93 (dd, J=8 and 3 Hz:1H); from 5.50 to 5.65(mt:2H); from 5.65 to 5.80(mt:2H); 5.81 (dd, J=16.5 and 1.5 Hz:1H); 6.11(d, J=16 Hz:1H); 6.51(dd, J=16.5 and 5 Hz:1 H); 7.23(mt:1H); 8.42(s:1H).

16,17-Dehydro-16-trifluoromethanesulphonyloxypristinamycin II$_B$ was prepared in the following manner:

5 cm$^3$ of diisopropylethylamine and 2.3 cm$^3$ of triflic anhydride were added, at −70° C. under an argon atmosphere, to 5 g of pristinamycin II$_B$ dissolved in 210 cm$^3$ of dichloromethane. After stirring for 2.5 hours at −74° C., the reaction mixture was poured into 200 cm$^3$ of saturated aqueous sodium bicarbonate solution. The organic phase was separated out after settling had taken place and was then washed with 200 cm$^3$ of saturated aqueous sodium chloride solution. The organic phase was separated out after settling had taken place, dried over magnesium sulphate, filtered and then concentrated to dryness under reduced pressure (2.7 kPa) to give 6.2 g of a residue, which was purified by flash chromatography on silica [eluent: dichloromethane/ethyl acetate (1/1 by volume)]. After concentrating the fractions containing the expected product, a solid was obtained, which was stirred in 60 cm$^3$ of a pentane/ethyl ether mixture (1/1 by volume) and then filtered off and dried under reduced pressure (2.7 kPa) to give 2.1 g of 16,17-dehydro-16-trifluoromethanesulphonyloxypristinamycin II$_B$ in the form of a white solid that melted at about 140° C. with decomposition.

$^1$H NMR spectrum (400 MHz, CDCl$_3$, δ in ppm): 0.96(d, J=6.5 Hz:3H); 0.99(d, J=6.5 Hz:3H); 1.08(d, J=6.5 Hz:3H); from 1.70 to 2.05(mt:4H); 1.80 (s:3H); 2.17(mt:1H); 2.76 (mt:1H); 3.13(dd, J=15 and 5.5Hz:1H); 3.46(mt:1H); 3.46 (mt:1H); 3.60(dd, J=15 and 6.5 Hz:1H); 3.72(mt:1H); 3.96 (mt:1H); 4.38 (mt:1H); 4.73(dd, J=10 and 2 Hz:1H); 4.80 (dd, J=8.5 and 4 Hz:1H); 4.90(mt:1H); 5.61(broad d, J=9 Hz:1H); from 5.75 to 5.85(mt:1H); 5.78(dd, J=16 and 1.5 Hz:1H); 6.05(mt:1H); 6.09(d, J=16.5Hz:1H); 6.52(dd, J=16 and 5.5 Hz:1H); 6.56 (s:1H); 8.19(s:1H).

EXAMPLE 2

(16R)-16-Cyano-16-deoxopristinamycin II$_B$:

(16S)-16-Cyano-16-deoxopristinamycin II$_B$:

A solution of 2.5 g of 16-cyano-16,17-deoxopristinamycin II$_B$ in 375 cm$^3$ of a buffer solution prepared before by degassing, under argon for 15 minutes, a solution of 21.7 g of tetraethylammonium tetrafluoroborate, 26.2 g of tetraethylammonium acetate tetrahydrate and 5.7 cm$^3$ of acetic acid, was transferred under an argon atmosphere into a 1000 cm$^3$ electrolysis tank (potentiostat-galvanostat: 555AAmel; integrator: 731 Amel; millivoltmeter: minisis 6000 Tacussel; working electrode: sheet of mercury of about 5 cm$^2$, contact by platinum wire dipping into the mercury via a side tube closed off by a spherical ground joint; reference electrode (Ag/AgCl): ECS; counter electrode: platinum wire wound in a spiral dipping into the electrolyte, separated from the cathode compartment by a nonwoven Nafion 125 cationic membrane; the membrane was placed at the end of a threaded tube and attached by a threaded Teflon stopper, a Teflon seal ensures leaktightness; modified glass metrohm cell (working volume ranging from 10 cm$^3$ to 60 cm$^3$ depending on the test) and degassed under argon for 15 minutes. A potential difference of −1.5 V (I=250 mA) was applied for 3 hours (consumption=906 coulombs). The reaction mixture was removed from the electrolysis tank and then concentrated to dryness under reduced pressure (2.7 kPa). The residue, to which was added another residue obtained from an identical test using 2 g of 16-cyano-16,17-dehydro-16-deoxopristinamycin II$_B$, was taken up in 500 cm$^3$ of ethyl acetate. This organic phase was successively washed with 200 cm$^3$ of pH7 buffer solution, 150 cm$^3$ of water, 100 cm$^3$ of pH7 buffer solution and then dried over magnesium sulphate, filtered and concentrated to dryness under reduced pressure (2.7 kPa) and gave 4.25 g of an orange-yellow solid, to which were added 2.6 g of a yellow solid obtained from an identical test (using 2.79 g of 16-cyano-16,17-dehydro-16-deoxopristinamcin II$_B$). After purification by flash chromatography on silica [eluent: dichloromethane/acetonitrile/methanol (92/4/4 by volume)] and concentrating the fractions containing the expected products, 2 solids were obtained, which were stirred in 10 cm$^3$ of diethyl ether and then filtered off and dried under reduced pressure to give, respectively, 0.73 g of the A isomer of 16-cyano-16-deoxopristinamycin II$_B$, in the form of a pale yellow powder that melted at about 130° C. (dec.) and 0.725 g of the B isomer of 16-cyano-16-deoxopristinamycin II$_B$, in the form of a yellow powder that melted at about 130° C. with decomposition.

A isomer: $^1$H NMR spectrum (400 MHz, CDCl$_3$, δ in ppm). 0.96(d, J=6.5 Hz:3H); 0.99(d, J=6.5 Hz:3H); 1.09(d, J=6.5 Hz:3H); from 1.70 to 2.05(mt:5H); 1.82(s:3H); 2.13 (mt:1H); 2.22(d, J=3.5 Hz: 1H); 2.43(ddd, J=16–10 and 4 Hz:1H); 2.75(mt:1H); 3.08(dd, J=16 and 5 Hz:1H); 3.21(dd, J=16 and 6 Hz:1H); 3.30(mt:1H); 3.49(ddd, J=15–10 and 4 Hz:1H); 3.92(mt:2H); 4.36 (ddd, J=15–8 and 4 Hz:1H); from 4.70 to 4.85(mt:2H); 4.96(mt:1H); 5.55(broad d, J=9 Hz:1H); 5.68(ddd, J=16–10 and 4 Hz:1H); 5.78(dd, J=16 and 1.5 Hz:1H); 5.94 (broad dd, J=8 and 4 Hz:1H); 6.19 broad d, J=16 Hz:1H); 6.54(dd, J=16 and 5 Hz:1H); 8.14 (s:1H).

B isomer: $^1$H NMR spectrum (400 MHz, CDCl$_3$, δ in ppm). 0.96(d, J=6.5 Hz:3H); 1.01(d, J=6.5Hz:3H); 1.10(d, J=6.5 Hz:3H); 1.61 (ddd, J=15–10 and 4 Hz:1H); from 1.75 to 2.05(mt:4H); 1.91(s:3H); 2.09(d, J=4 Hz:1 H); from 2.05 to 2.30(mt:2H); 2.77(mt:1H); 2.92(dd, J=16 and 5.5 Hz:1H); from 3.20 to 3.35(mt:2H); 3.49(mt:1H); 3.86(mt:1H); 4.10 (mt:1H); 4.56(mt:1H); from 4.75 to4.90(mt:1H);4.79(dd, J=10 and 1.5 Hz:1H); 4.84(dd, J=9 and 4 Hz; 1 H); 5.36 (broad d, J=9 Hz:1H); 5.77(ddd, J=16–8.5 and 4 Hz:1H); 5.83(dd, J=16 and 1.5 Hz:1H); 6.02(broad dd, J=9 and 3 Hz:1H); 6.21(large d, J=16 Hz:1H); 6.53 (dd, J=16 and 5 Hz:1H); 8.16(s:1H).

16-cyano-16,17-dehydro-16-deoxopristinamycin II$_B$ was prepared in the following way:

A solution of 2.3 g of 16,17-dehydro-16-trifluoromethanesulphonyl-oxypristinamycin II$_B$ (prepared as described in Example 1), 0.36 g of potassium cyanide, 0.16 g of tetrakis(triphenylphosphine)palladium and 0.53 g of copper iodide in 25 cm$^3$ of acetonitrile were refluxed under an argon atmosphere. After stirring for 4 hours, the reaction mixture was filtered through Celitee® and the filtrate was concentrated to dryness under reduced pressure (2.7 kPa). The residue was taken up in 50 cm³ of dichloromethane and washed twice with 40 cm³ of water. The organic phase was dried over magnesium sulphate, filtered and then concentrated to dryness under reduced pressure (2.7 kPa) to give 2 g of an ochre-colored foam, which was purified by two successive flash chromatographies on silica [eluent: dichloromethane/acetonitrile/methanol (96/2/2 by volume) and then a dichloromethane/acetonitrile/methanol gradient (100/0/0 to 96/2/2 by volume)]. After concentrating the fractions containing the expected product, a solid was obtained, which was stirred in 10 cm³ of diethyl ether and then filtered off and dried under reduced pressure (2.7 kPa) to give 0.19 g of 16-cyano-16,17-dehydro-16-deoxopristinamycin II$_B$ in the form of a pale yellow solid that melted at about 142° C. with decomposition.

¹H NMR spectrum (400 MHz, CDCl$_3$, δ in ppm): 0.96(d, J=6.5 Hz:3H); 1.00(d, J=6.5 Hz:3H); 1.08(d, J=6.5 Hz:3H); from 1.70 to 2.05(mt:4H); 1.78(d, J=5Hz:1H); 1.82(s:3H); 2.16(mt:1H); 2.78(mt:1H); 3.03(dd, J=14 and 5 Hz:1H); from 3.40 to 3.50(mt:1H); 3.50(dd, J=14 and 6.5 Hz:1H); 3.72 (mt:1H); 3.96 (mt:1H); 4.36(ddd, J=16–9 and 4 Hz:1H); 4.72(dd, J=10 and 2 Hz:1H); 4.80 (dd, J=9 and 4.5 Hz:1H); 4.91(mt:1H); 5.58(broad d, J=9 Hz:1H); 5.77 (dd, J=16 and 1.5 Hz:1H); 5.79(ddd, J=16–9 and 4 Hz:1H); 6.00(broad dd, J=9 and 5 Hz:1H); 6.10(broad d, J=16 Hz:1H); 6.51(dd, J=16 and 5 Hz:1H); 7.08(s:1H); 8.26 (s:1H).

The present invention also relates to pharmaceutical compositions containing at least one streptogramin group A derivative according to the invention, in pure form, combined with at least one group B streptogramin derivative, where appropriate in the form of a salt, and/or in the form of a combination with at least one compatible and pharmaceutically acceptable diluent or adjuvant.

The compositions according to the invention may be used orally, parenterally, topically, rectally or as aerosols.

Solid compositions for oral administration which may be used include, for example, tablets, pills, gel capsules, powders and granules. In these compositions, the active product according to the invention, generally in the form of a combination, can be mixed with at least one inert diluent or adjuvant, such as sucrose, lactose, or starch. These compositions may comprise substances other than diluents, for example, a lubricant such as magnesium stearate or a coating intended for controlled release.

Liquid compositions for oral administration which may be used include, for example, pharmaceutically acceptable solutions, suspensions, emulsions, syrups, and elixirs containing inert diluents such as water or liquid paraffin. These compositions may also comprise substances other than diluents, such as, for example, wetting, sweetening, or flavoring products.

The compositions for parenteral administration may be, for example, sterile solutions or emulsions. Solvents or vehicles which may be used include, for example, propylene glycol, polyethylene glycol, plant oils, such as, for example, olive oil, and injectable organic esters, for example, ethyl oleate. These compositions may also comprise at least one adjuvant, such as, for example, adjuvants chosen from wetting agents, isotonic agents, emulsifiers, dispersants, and stabilizers.

The sterilization may be carried out in several ways, for example using a bacteriological filter, by irradiation or by heating. The compositions may also be prepared in the form of sterile solid compositions which may be dissolved at the time of use in sterile water or any other injectable sterile medium.

The compositions for topical administration may be, for example, creams, ointments, lotions or aerosols.

The compositions for rectal administration may be, for example, suppositories or rectal capsules which contain, besides the active principle, excipients such as cocoa butter, semisynthetic glycerides or polyethylene glycols.

The compositions may also be aerosols. For use in the form of liquid aerosols, the compositions may be stable sterile solutions or solid compositions dissolved at the time of use in apyrogenic sterile water, in saline or any other pharmaceutically acceptable vehicle. For use in the form of dry aerosols for direct inhalation, the active principle can be finely divided and combined with a solid water-soluble diluent or vehicle with a particle size ranging from, for example 30 to 80 μm, for example, dextran, mannitol or lactose.

In human therapy, for example, the novel streptogramin derivatives according to the invention can be used for treating infections of bacterial origin. The doses depend on the desired effect and the duration of the treatment. The doctor will determine the dosage (s)he considers to be most suitable depending on the treatment, as a function of the age, weight, degree of infection and the other factors specific to the individual to be treated. Generally, for example, the doses can range from 0.5 to 3 g of active product in 2 or 3 administrations per day, via the oral or parenteral route for an adult.

The example which follows illustrates a composition according to the invention, without however exhibiting a limiting character.

EXAMPLE A

Tablets containing a 250 mg dose of active product and having the composition below can be prepared according to known, art-recognized techniques:

| | |
|---|---|
| (16R)-16-cyano-16-deoxopristinamycin II$_B$ | 175 mg |
| Pristinamycin I$_B$ | 75 mg |
| Excipient: starch, hydrated silica, dextrin, gelatin, magnesium stearate: qs | 500 mg |

EXAMPLE B

Tablets containing a 250 mg dose of active product and having the composition below can be prepared according to known, art-recognized techniques:

| | |
|---|---|
| (16S)-16-cyano-16-deoxopristinamycin II$_B$ | 175 mg |
| Pristinamycin I$_B$ | 75 mg |
| Excipient: starch, hydrated silica, dextrin, gelatin, magnesium stearate: qs | 500 mg |

What is claimed is:

1. A group A streptogramin compound of formula (I) or a salt thereof:

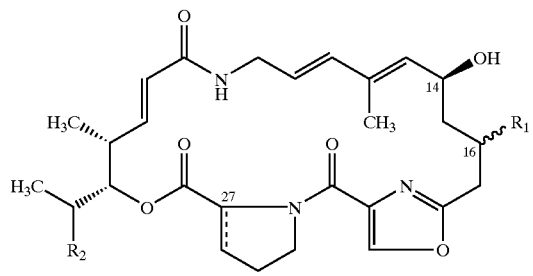

(I)

wherein:
- $R_1$ is chosen from cyano and ethynyl groups,
- $R_2$ is chosen from a hydrogen atom, a methyl group, and an ethyl group, and the bond

----- is a single bond (27R stereochemistry) or a double bond.

2. A group A streptogramin compound of formula (I) or a salt thereof according to claim 1, wherein:
- $R_1$ is chosen from a cyano group and an ethynyl group,
- $R_2$ is a methyl group, and
- the bond

----- is a single bond (27R stereochemistry) or a double bond.

3. A process for preparing a group A streptogramin compound of formula (I) or a salt thereof according to claim 1, said process comprising:

reacting a 16-sulphonyloxy compound of formula (II):

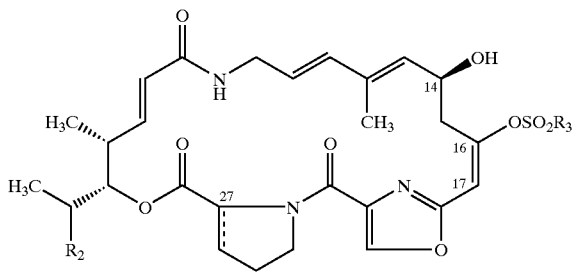

(II)

wherein:
- $R_2$ is chosen from a hydrogen atom, a methyl group, and an ethyl group,
- $R_3$ is a perfluoroalkyl group comprising from 1 to 10 carbon atoms, and
- the bond

----- is a single bond (27R stereochemistry) or a double bond, with an alkali metal cyanide, reducing the compound obtained from said reaction, and optionally separating the 16R and 16S isomers obtained from said reduction.

4. A process for preparing a group A streptogramin compound of formula (I) or a salt thereof according to claim 1, said process comprising: carbonylating a 16-sulphonyloxy compound of formula (II):

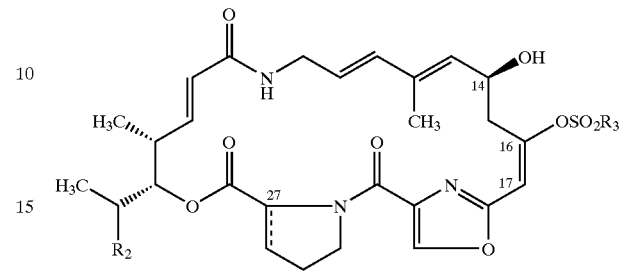

(II)

wherein:
- $R_2$ is chosen from a hydrogen atom, a methyl group, and an ethyl group,
- $R_3$ is a perfluoroalkyl group comprising from 1 to 10 carbon atoms, and
- the bond

----- is a single bond (27R stereochemistry) or a double bond, to form a lactone of formula (III):

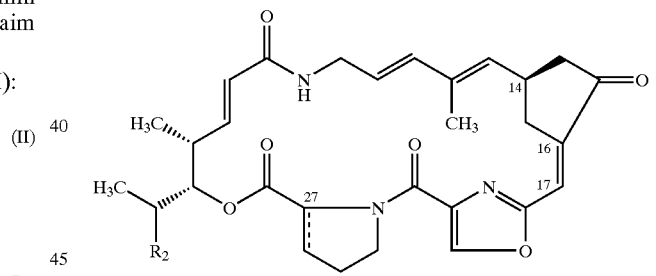

(III)

wherein:
- $R_2$ is chosen from a hydrogen atom, a methyl group, and an ethyl group, and
- the bond

----- is a single bond (27R stereochemistry) or a double bond, reducing said lactone to a lactol, reacting said lactol with dimethyl diazomethylphosphonate or dimethyl 1-diazo-2-oxopropylphosphonate, and optionally separating the 16R and 16S isomers obtained.

5. A process according to claim 4, wherein said R3 group is chosen from a trifluoromethyl group and a nonfluorobutyl group.

6. A group A streptogramin compound of formula (II) or a salt thereof:

(II)

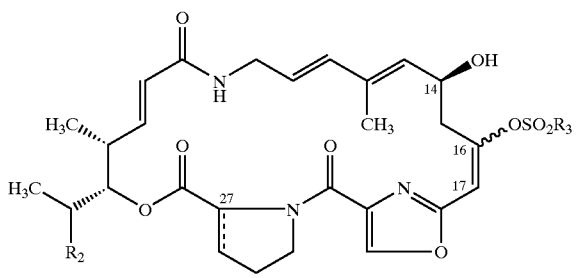

wherein:
  R₂ is chosen from a hydrogen atom, a methyl group, and an ethyl group,
  R₃ is a perfluoroalkyl group comprising from 1 to 10 carbon atoms, and
  the bond

----- is a single bond (27R stereochemistry) or a double bond.

7. A group A streptogramin compound of formula (II) or a salt thereof according to claim 6, wherein said R₃ group is chosen from a trifluoromethyl group and a nonafluorobutyl group.

8. A process for preparing a group A streptogramin compound of formula (II) or a salt thereof according to claim 6, said process comprising:
  reacting a fluoride or an anhydride, wherein said fluoride or said anhydride comprises a perfluoroalkyl group comprising from 1 to 10 carbon atoms, with a streptogramin compound of formula (IV):

(IV)

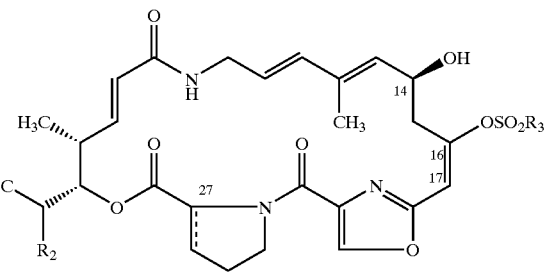

wherein:
  R₂ is chosen from a hydrogen atom, a methyl group, and an ethyl group, and
  the bond

----- is a single bond (27R stereochemistry) or a double bond, in the presence of a base.

9. A group A streptogramin compound of formula (III) or a salt thereof:

(III)

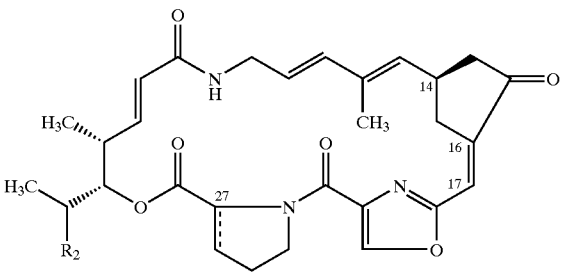

wherein:
  R₂ is chosen from a hydrogen atom, a methyl group, and an ethyl group, and
  the bond

----- is a single bond (27R stereochemistry) or a double bond.

10. A process for preparing a group A streptogramin compound of formula (III) or a salt thereof according to claim 9, said process comprising:
  carbonylating a 16-sulphonyloxy compound of formula (II):

(II)

wherein:
  R₂ is chosen from a hydrogen atom, a methyl group, and an ethyl group,
  R₃ is a perfluoroalkyl group comprising from 1 to 10 carbon atoms, and
  the bond

----- is a single bond (27R stereochemistry) or a double bond.

11. A pharmaceutical composition comprising a pharmaceutically effective amount of at least one group A streptogramin compound of formula (I) or salt thereof according to claim 1 and at least one agent chosen from pharmaceutically acceptable diluents and pharmaceutically acceptable adjuvants.

* * * * *